United States Patent [19]

Maggard

[11] Patent Number: 4,963,745

[45] Date of Patent: Oct. 16, 1990

[54] OCTANE MEASURING PROCESS AND DEVICE

[75] Inventor: Steven M. Maggard, Huntington, W. Va.

[73] Assignee: Ashland Oil, Inc., Ashland, Ky.

[21] Appl. No.: 402,959

[22] Filed: Sep. 1, 1989

[51] Int. Cl.$^5$ ............................................. G01N 21/59
[52] U.S. Cl. ................................... 250/343; 250/341; 250/339
[58] Field of Search ........................ 250/343, 341, 339

[56] References Cited

U.S. PATENT DOCUMENTS 4,800,279 1/1989 Hieftje et al. ...................... 250/339

FOREIGN PATENT DOCUMENTS 285251 10/1988 European Pat. Off. ............ 250/343

OTHER PUBLICATIONS

"Near-Infrared Reflectance Analysis by Gauss-Jordan Linear Algebra", D. E. Honigs, J. M. Freelin, G. M. Hieftje, T. B. Hirschfeld, Applied Spectroscopy, vol. 37, No. 6, 1983, pp. 491-497.

"Prediction of Gasoline Octane Numbers from Near Infrared Spectral Features in the Range 660-1215 nm", by J. J. Kelly et al., Analytical Chemistry, vol. 61, No. 4, Feb. 15, 1989, pp. 313-320.

Primary Examiner—Carolyn E. Fields
Attorney, Agent, or Firm—Richard C. Willson, Jr.

[57] ABSTRACT

The near infrared absorbance of the methyne band measures octane (pump, RON, and MON) with excellent correlation and can be used for gasoline blending. The absorbance may be measured as the first, second, third, fourth or higher derivative or by other signal processing techniques. The signal can be used to control a multi-component gasoline blending system to produce a preset desired octane. Such continuous or frequent measurement of octane (research octane number, RON; motor octane number, MON; and pump octane number (research plus motor times 0.5)) permits constant or frequent optimization of gasoline blending to produce a target octane which is sufficient to meet motorists' needs, yet uses minimum amounts of the more expensive high octane blending stocks.

18 Claims, 6 Drawing Sheets

OCTANE MEASURING PROCESS AND DEVICE

BACKGROUND OF INVENTION

Because the well known knock engine method of measuring fuel octane or other measure of knock avoidance is not continuous, requires an internal combustion engine under load, and involves spark hazard and substantial maintenance; a continuous method for measurement of octane number, etc. has long been sought.

Kelly, Barlow, Jinguji and Callis of the University of Washington, Seattle, (Analytical Chem. 61, 313–320,) found gasoline octane numbers could be predicted from near infrared absorbance in the range 660–1215 nanometers (nm). They found best correlation between absorbance and octane number to occur at 896, 932 and 1164 nm for research octane number, 930, 940 and 1012 nm for motor octane number, and 896, 932 and 1032 nm for pump octane number.

A search in Lexpat (U.S. patents from 1975 forward) under infrared, octane, and (gasoline or fuel) within 25 words of each other showed only four patents: U.S. Pat. Nos. 4,277,326; 4,264,336; 3,496,053; and 903,020, none of which relate to new techniques for the measurement of octane.

The present invention, by measurement of absorbance in a range close to but above the Kelly et al. wavelengths, shows dramatically improved correlation as compared to measurements made in the wavelengths described by Kelly et al.

SUMMARY OF THE INVENTION

According to the present invention, any of the three octane numbers (or all of them) can be measured (predicted) by measuring the near infrared absorbance in the methyne range (1200 to 1236 nm). This range correlates sufficiently closely to permit in-line (or at-line, measuring a smaller sidestream) measurement to control blending systems to produce gasolines of target octane with close accuracy.

Preferably, the absorbance in the methyne range is converted into an electrical signal which is preferably combined with signals indicative of absorbance in other ranges, most preferably about 1196 nm and 1236 nm.

Octane

As mentioned above, the present invention is useful for the measurement and control of systems producing octanes according to the well known knock engine procedures for RON, MON, and pump [(R+M)/2] octane. Pump octanes measured are preferably in the range of from about 75 to 120, and most preferably from about 84 to 95.

Signal Processing

As those skilled in the art will be aware, the absorbance signal from the measurement of the methyne and other bands will preferably be mathematically processed to provide derived signals which are more directly indicative of the octane being measured. Preferred techniques for mathematical processing are the first, second, third, and fourth or higher derivative. The technique of dividing the absorbance at one wavelength by the absorbance at all other wavelengths in order to cancel out background or noise and normalize the signal; spectral subtraction in which the spectrum of one sample is subtracted from the spectrum of another sample in order to differentiate differences in absorbance, and various combinations of these mathematical techniques. Also valuable are well known curve fitting techniques, e.g. Savitsky-Golay curve fit, Kubelka-Munk curve fit transformation, and n-point smoothing (signal averaging).

Theory

While the invention is claimed independent of any underlying theory, the invention appears to relate to the free radical propagation and stability of the fuel being analyzed. It is hypothesized that ease and smoothness of combustion are probably related to the free radical stability of the species generated during the process of combustion, e.g. secondary and tertiary free radicals. The methyne band, along with the tertiary butyl band (1200–1236 nm), is indicative of methyne groups and t-butyl groups, respectively. The presence of methyne groups and t-butyl groups affords a source of stable free radicals which smooth the combustion process in contrast to the less stable compounds which give rise to sudden changes in combustion which result in knocking of the internal combustion engine in which the fuel is being consumed. Octane is the measure of the ability of the engine to run under adverse circumstances and heavy loads without substantial knocking. 1985 *Annual Book of ASTM Standards*, Volume 05.04 Test Methods for Rating Motor, Diesel and Aviation Fuels, American Society for Testing and Materials; Philadelphia, Pa., 1985.

Analytical Equipment

Near Infrared spectrometers and modified IR spectrometers of convention design may be used with the invention. Preferred modes of operation are transmission, reflectance, and transreflectance. Suitable spectrometers are the NIRSystems Model 6500; LT Industries Model 1200; and the Guided Wave Model 300 Series. The spectrometer can be operated on a batch basis (receiving signals, e.g. by a sample feeding arrangement), or, more preferably, on a continuous basis in which the fluid to be measured flows through a cell or a probe immersed in the flowing fluid transmits optically through a fiber-optic cable to the spectrophotometer. The techniques for sampling, measuring, and signal processing can be conventional and are well known to those skilled in the art.

Blending Systems

Blending systems for use with the present invention can be of conventional design, usually involving the use of proportioning pumps or automatic control valves which control the addition rate for each of a series of components fed from different tanks or other sources. A computer receiving the output signal from the spectrophotometer can readily process the information to not only provide the target octane number in the finished blended gasoline, but also to provide the target octane at minimum cost, given the relative costs and octane enhancement values of the components being fed to the blending system.

Utility of the Invention

As described above, the invention will be useful in the blending of gasoline, less preferably diesel fuels (cetane number) and jet fuels, e.g. JP4, both in refineries and in large fuel storage terminals. Blending can be into storage tanks, tank trucks, rail cars, barges, or other transportation vehicles. An allowance for octane depletion during transportation based on expected weather conditions can also be included in determining the target octane for blending. Additionally, the invention will be useful for monitoring gasoline quality at retail outlets to assure quality control specifications.

DESCRIPTION OF THE PREFERRED EMBODIMENTS

EXAMPLE I

A series of samples of about 141 blended gasolines are analyzed for pump octane number (RON plus MON divided by 2) by measuring the near IR absorbance at 1220, 1196, and 1236 nm. The second derivative is taken of each absorbance measured and is used to perform a multiple regression. The multiple regression analysis of the data essentially fits the curve;

$$Y = K(0) + K(1) \times \text{second derivation of absorbance at 1220 nm}$$
$$+ K(2) \times \text{second derivation of absorbance at 1196 nm}$$
$$+ K(3) \times \text{second derivation of absorbance at 1236 nm}$$

all as shown in Table A.

TABLE A

| File name: | OCT2ND | Regression Results |
|---|---|---|
| Instrument: | 6500 | Standard error = .345 |
| No. of spectra: | 141 | Multiple R = .9927 |
| Constituent: 3, | PUMP | |
| Math: | 2nd derivative | |
| Segment: | 20 | |
| Gap: | 0 | |

TABLE A-continued

| Constants | Wavelength | Simple R |
|---|---|---|
| K(0) = 85.506 | | |
| K(1) = 70.323 | 1220 | .988 |
| K(2) = 16.465 | 1196 | .385 |
| K(3) = 28.615 | 1236 | −.951 |

The multiple coefficent of correlation between the octane, y, and the second derivatives of the absorbances is 0.9927, a very close correlation. This is equivalent to a standard error of about plus or minus 0.345 octane numbers which is better than can generally be accomplished by a knock engine with a skilled operator (the average of ASTM methods 2699-84 and 2700-84).

EXAMPLE II

Figure 1:
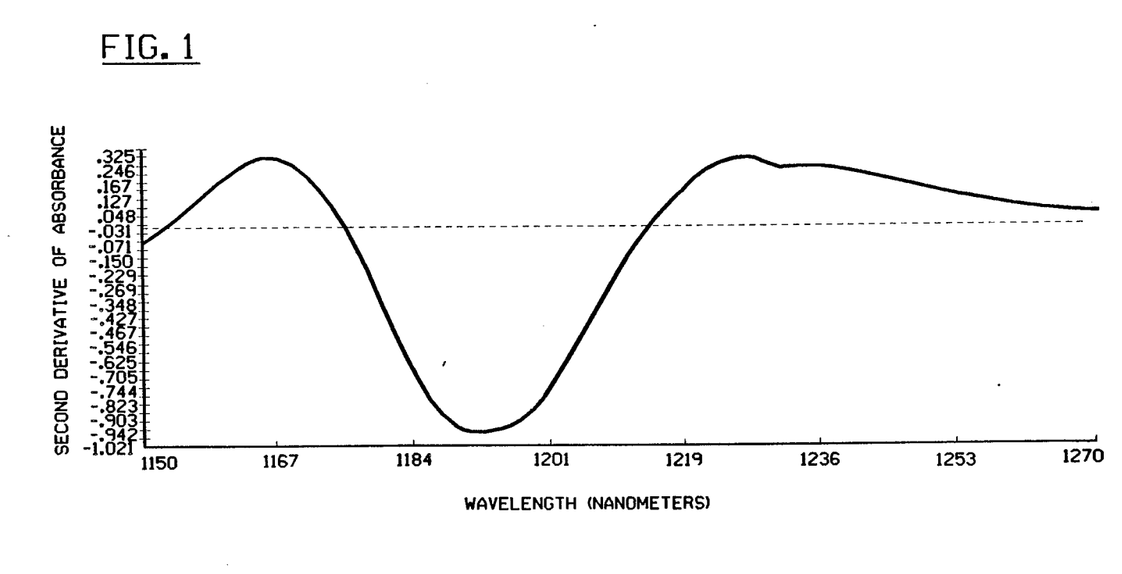
FIG. 1 is a plot of the preferred second derivative of absorbance versus wavelength ($d^2A/d$, nanometers) and shows the near infrared band assignments for the methyl, methyne, t-butyl and methylene functional groups.
Figure 2:
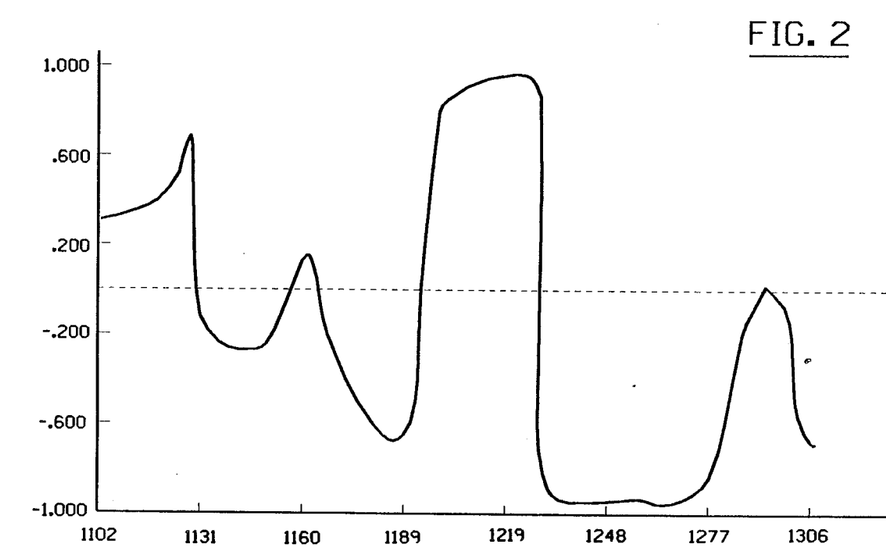
FIG. 2 is a plot of multiple correlation versus wavelength, showing the excellent correlation obtained with the methyne and t-butyl groups. Note the change in the correlation at 1228 nm from strongly positive to negative as the scan proceeds from the t-butyl and methyne groups to the methylene.
Figure 3:
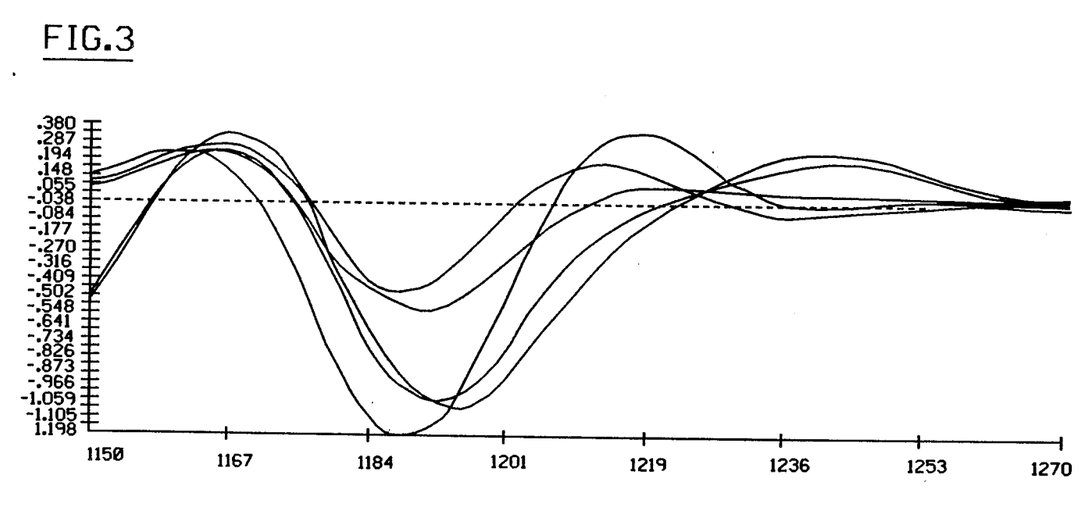
FIG. 3 shows the second derivative of the methyne and methyl absorption bands in the near infrared versus the wavelength for some selected compounds. Note the cumene and 2,3,4-trimethyl pentane do not contain methylene groups. This demonstrates that the methyne band position in the second derivative spectrum extends from 1202 to 1236 nm.
Figure 4:
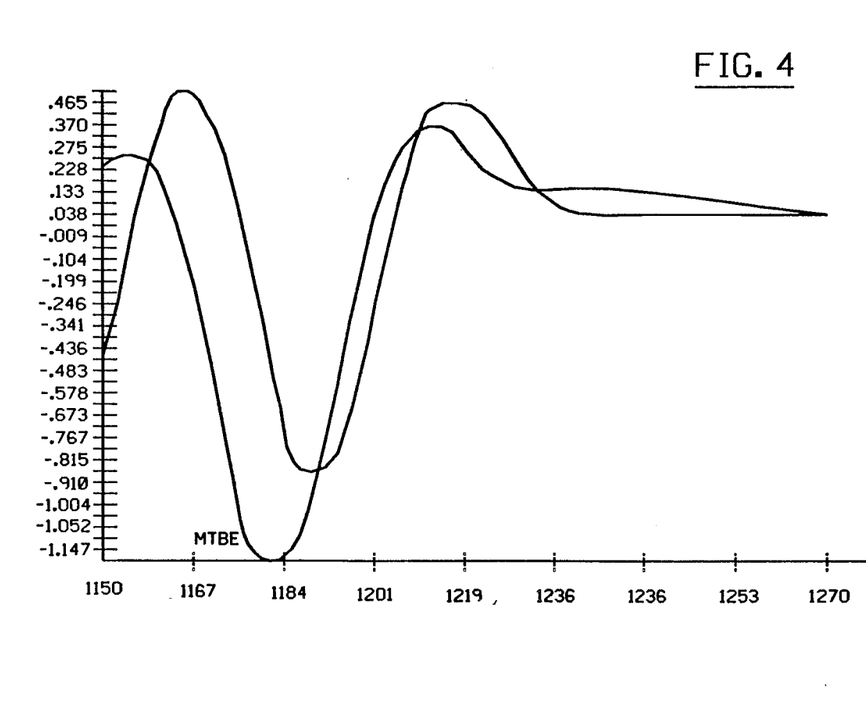
FIG. 4 similarly shows that t-butyl group (e.g. of the methyl tertiary butyl ether, MTBE, a popular gasoline octane enhancer additive) also falls within the methyne absorption range. The t-butyl band is centered between 1200–1232 nm.

FIG. 1 shows a plot of the second derivative of the near infrared absorption spectra of approximately 142 gasoline samples, analyzed by the techniques of Example I. Also plotted on FIG. 1 are the second derivative ranges of the methyl (1174 to 1212 nm), t-butyl/methyne (1212 to 1228 nm), and the methylene (1228 to about 1268 nm). These absorptions are in the second overtone region of the near infrared spectrum. That is, the original absorbance band for the methyl, methyne, t-butyl and methylene groups is at about 3367 nm, so these near infrared ranges being measured are overtones similar to harmonics of the original bands. Working in the second overtone has advantages over the third overtone which was used by Kelly et al. For example, at a total path length of 20 mm, the absorbance measurements in the second overtone region are in the region where the Beer-Lambert Law is obeyed, whereas in the third overtone region they are not. (Note, Kelly et al used a 20 mm path length, 10 mm cell in reflectance mode.)

EXAMPLE III

Table B shows techniques similar to those used in Example I, but utilizing only the 1220 nm wavelength (methyne range). The multiple correlation is 0.9836 and is the highest correlation of any single wavelength in the near infrared range (800–2500 nm) with motor octane number.

TABLE B

| File name: | OCT2ND | Regression Results |
|---|---|---|
| Instrument: | 6500 | Standard error = .524 |
| No. of spectra: | 141 | Multiple R = .9836 |
| Constituent: 2, | MON | |
| Math: | 2nd derivative | |
| Segment: | 20 | |
| Gap: | 0 | |
| Constants | Wavelength | Simple R |
| K(0) = 75.158 | | |
| K(1) = 59.949 | 1220 | .984 |

EXAMPLE IV

When techniques similar to those described in Example III on research octane number, the correlation between RON and the second derivative of absorbance at the 1220 nm wavelength is 0.9649 indicating a standard error of plus or minus 0.752 octane numbers, the best correlation and lowest standard error available with any single wavelength in the near infrared range. (see Table C)

TABLE C

| | Regression Results | |
|---|---|---|
| File name: | OCT2ND | |
| Instrument: | 6500 | Standard error = .752 |
| No of spectra: | 141 | Multiple R = .9649 |
| Constituent: 1, | RON | |
| Math: | 2nd derivative | |
| Segment: | 20 | |
| Gap: | 0 | |
| Constants | Wavelength | Simple R |
| K(0) = 84.408 | | |
| K(1) = 57.980 | 1220 | .965 |

EXAMPLE V

When techniques similar to those described in Example III are used to determine pump octane number, the correlation between RON and the second derivative of absorbance at the 1220 nm wavelength is 0.9878 indicating a standard error of plus or minus 0.442 pump octane numbers, the best correlation and lowest standard error available with any single wavelength in the near infrared range. (see Table D)

TABLE D

| | Regression Results | |
|---|---|---|
| File name: | OCT2ND | |
| Instrument: | 6500 | Standard error = .442 |
| No. of spectra: | 141 | Multiple R = .9878 |
| Constituent: 3, | PUMP | |
| Math: | 2nd derivative | |
| Segment: | 20 | |
| Gap: | 0 | |
| Constants | Wavelength | Simple R |
| K(0) = 79.782 | | |
| K(1) = 58.962 | 1220 | .988 |

EXAMPLE VI

Figure 5:
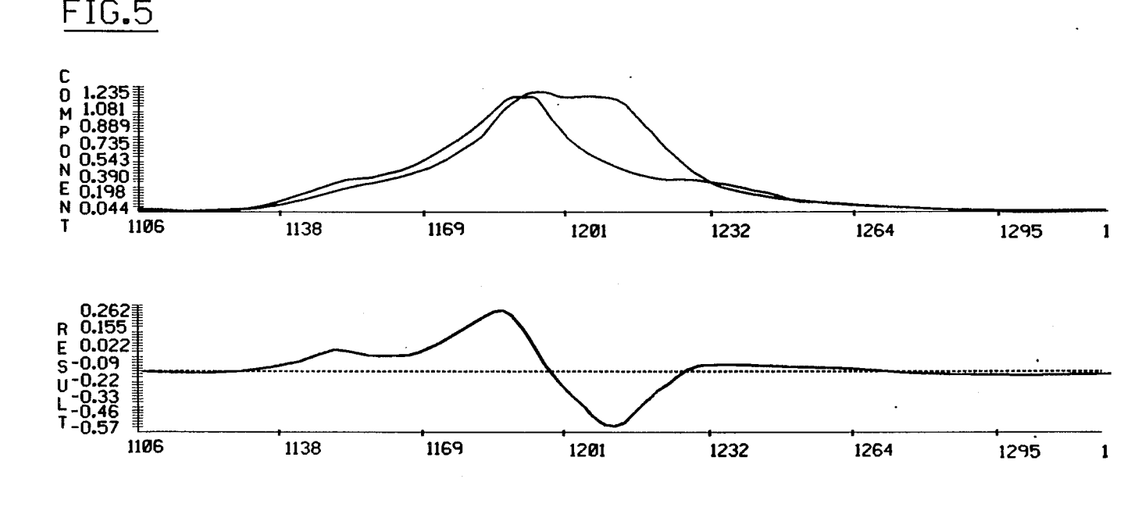
FIG. 5 is the Savistsky-Golay curve fit of the spectrum of 2,3,4-trimethyl pentane and 2-methyl pentane showing the methyne absorbance in the transmission spectrum.

FIG. 5 shows the results of subtracting the absorbance versus wavelength spectrum of n-hexane from 2,3,4-trimethyl pentane using a Savitski-Golay curve fit. From this figure, one can see that without mathematical treatment the methyl band extends from about 1160–1195 nm, the methylene band from about 1195–1200 nm, and the methyne band is from about 1230–1250 nm.

EXAMPLE VII

Comparative

When techniques similar to those described in Example III are used to determine pump octane number, but using the regression model and wavelengths of Kelly et al., the correlation between pump octane number and the second derivative of absorbance at the 896, 932 and wavelength is 0.9841 indicating a standard error of plus or minus 0.497 pump octane numbers (but using 90 samples) as set forth in Table E. Thus, the present invention with only a single wavelength measured provides accuracy better than the multiple correlation suggested by Kelly et al.

TABLE E

| (Kelly Wavelengths) | | |
|---|---|---|
| | Regression Results | |
| File name: | GASMINUS | |
| Instrument: | 6500 | Standard error = .497 |
| No. of spectra: | 90 | Multiple R = .9841 |
| Constituent: 1, | PUMP | |
| Math: | N-Point smooth | |
| Segment: | 2 | |

TABLE E-continued

| Gap: | 0 | |
|---|---|---|
| Constants | Wavelength | Simple R |
| K(0) = 100.105 | | |
| K(1) = 278.370 | 896 | .236 |
| K(2) = −768.856 | 932 | −.943 |
| K(3) = 305.203 | 1032 | −.453 |
| (Invention) | | |
| | Regression Results | |
| File name: | GAS2ND | |
| Instrument: | 6500 | Standard error = .414 |
| No. of spectra: | 90 | Multiple R = .9887 |
| Constituent: 3, | PUMP | |
| Math: | 2nd Derivative | |
| Segment: | 20 | |
| Gap: | 0 | |
| Constants | Wavelength | Simple R |
| K(0) = 79.756 | | |
| K(1) = 59.253 | 1220 | .989 |

EXAMPLE VIII

Figure 6:
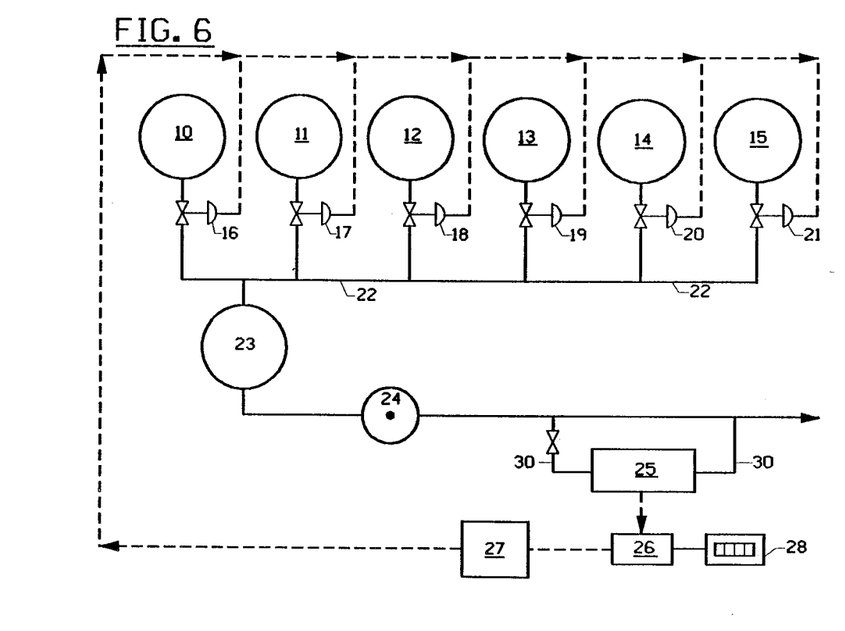
FIG. 6 is a schematic diagram of a gasoline blending system utilizing the octane measurement techniques of the present invention.

FIG. 6 is a schematic diagram of a typical gasoline blending system such as might be used to employ the present invention at a refinery or large terminal. Tanks 10 through 15 contain gasoline blending stocks, e.g. reformates, isomerates, alkylates, etc. Each of these components has its own octane value as well as a price. For example, reformate and alkylate are both high in octane number, but are relatively expensive blending stocks. Each of the tanks has an automatic control valve 16 through 21 which controls the flow of the particular blending stock from the tank into a common header 22 and thence into mixing tank 23 from which pump 24 moves the blended gasoline through "at-line" analyzer 25 which analyzes the near IR absorbance of a sidestream 30 at 1220 nm, 1196 nm, and 1236 nm, and transmits the resulting absorbance measurements to a mathematical conversion device 26 which converts the signal into the second derivative and feeds the resulting signal to computer 27. Optional display device 28 can display both the target octane and the measured octane number at all times. The output from computer 27 is fed to each individual control valve (or proportioning pump) 16 through 21, and controls the relative flow of each of the gasoline blending components 10 through 15 into the blending tank 23. Various adjustments can be made for hold-up in the tank, etc. (Alternately, the functions of the mathematical conversion device 26 can also be performed by computer 27.)

The resulting gasoline is within plus or minus approximately 0.3 octane numbers at all times.

In another variation, each of the lines from the gasoline blending stock tanks 10–15 is fitted with a near IR analyzer (like 25) which inputs a signal to the computer 27 which is now programmed to control and optimize the blending process based on all these inputs.

In another variation, an operator reads the computer output of octane number and manually or mechanically controls and optimizes the blending process.

Modifications

Specific compositions, methods, devices or embodiments discussed are intended to be only illustrative of the invention disclosed by this specification. Variation on these compositions, methods, or embodiments will be readily apparent to a person of skill in the art based upon the teachings of this specification and are therefore intended to be included as part of the inventions disclosed herein. For example, individual variations of NIR spectrometers could cause the optimal wavelengths to be shifted slightly since the precise location of any wavelength is inexact. Also, since differing crude oils produce gasolines which are of differing molecular structures, it is highly likely that a different wavelength might show higher correlations for the selection of the initial wavelength. It should be noted that the methyne group could still be valuable in conjunction with the first wavelength.

Reference made in the other specification is intended to result in such patents or literature being expressly incorporated herein by reference including any patents or other literature references cited within such patents.

What is claimed is:

1. In a process for the determining of octane number or other measure of knock avoidance of a fuel by near infrared range spectroscopy, the improvement comprising determining said octane number or other measure of knock avoidance by:
   a. measuring absorbance in the t-butylmethyne band;
   b. periodically or continuously outputting a periodic or continuous signal indicative of the intensity of said absorbance in said band or one mathematical function or a combination of mathematical functions thereof; and
   c. mathematically converting said signal to an output signal indicative of said octane number or other measure of knock avoidance of said fuel.

2. A process according to claim 1 wherein said fuel flows substantially intermittently or continuously past the point where said measurement is being made.

3. A process according to claim 1 wherein a derivative of said absorption of said t-butyl/methyne band is measured.

4. A process according to claim 3 wherein a derivative of said absorption of said t-butyl/methyne band is the first derivative.

5. A process according to claim 3 wherein a derivative of said absorption of said t-butyl/methyne band is the second derivative.

6. A process according to claim 3 wherein a derivative of said absorption of said t-butyl/methyne band is the third derivative.

7. A process according to claim 3 wherein a derivative of said absorption of said t-butyl/methyne band is the fourth or higher derivative.

8. A process according to claim 1 wherein the fuel is gasoline and the octane number measured is pump octane number.

9. A process according to claim 1 wherein the fuel is gasoline and the octane number measured is motor octane number.

10. A process according to claim 1 wherein the fuel is gasoline and the octane number measured is research octane number.

11. A process according to claim 1 wherein said signal controls a fuel blending system feeding blending components having different octane numbers into a common zone, whereby a fuel product having a desired octane number is produced.

12. A process according to claim 11 wherein each component is analyzed by a near infrared analyzer to produce a signal and all such signals are inputted to a computer controlling the blending process.

13. A processing according to claim 1 wherein said fuel is a gasoline.

14. A process according to claim 2 wherein said fuel is a gasoline.

15. A process according to claim 3 wherein said fuel is a gasoline.

16. A process according to claim 5 wherein said fuel is a gasoline.

17. A process according to claim 1 wherein absorbance in one or more additional bands is measured and a signal indicative of its respective absorbance is combined with said signal indicative of absorbance in said t-butyl/methyne band.

18. A process according to claim 17 wherein said one or more additional bands comprise at least one band selected from the group of methyl, methylene, aromatic and substituted aromatic bands.

* * * * *